(12) United States Patent
Chitnis et al.

(10) Patent No.: US 6,324,895 B1
(45) Date of Patent: *Dec. 4, 2001

(54) PROCESS FOR DETERMINING THE AMOUNT OF EROSIVE MATERIAL ENTERING A POWER RECOVERY TURBINE

(75) Inventors: Girish K. Chitnis, Fairfax, VA (US); Brent David Freeman, Joliet, IL (US); Edward A. Lemon, Jr., Westville; Stephen J. McGovern, Mantua, both of NJ (US); Lisa Mazzocato, Houston, TX (US)

(73) Assignee: Mobil Oil Corporation, Fairfax, VA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/023,808

(22) Filed: Feb. 13, 1998

(51) Int. Cl.$^7$ ..................................................... G01N 1/22
(52) U.S. Cl. ................. 73/28.04; 73/863.21; 73/864.81; 73/23.31
(58) Field of Search ..................... 73/863.21, 863.23, 73/863.41, 863.43, 863.58, 28.01, 28.04, 23.31, 864.81

(56) References Cited

U.S. PATENT DOCUMENTS

| | | | |
|---|---|---|---|
| 3,581,469 | * 6/1971 | Davis | 73/863.12 |
| 4,144,759 | * 3/1979 | Slowik | 73/863.58 |
| 4,355,539 | * 10/1982 | Schatz | 73/863.11 |
| 4,479,379 | * 10/1984 | Tarcy | 73/863.21 |
| 4,531,402 | 7/1985 | Reif et al. | 73/28 |
| 4,678,483 | * 7/1987 | Dolan et al. | 73/863.23 |
| 4,928,480 | 5/1990 | Oliver et al. | 60/39.092 |
| 5,078,758 | * 1/1992 | Maller et al. | 73/864.81 |
| 5,148,669 | 9/1992 | Sellakumar | 60/39.092 |
| 5,464,528 | 11/1995 | Owen et al. | 208/161 |
| 5,498,271 | 3/1996 | Marple et al. | 55/321 |
| 5,571,945 | 11/1996 | Koutrakis et al. | 73/28.03 |

OTHER PUBLICATIONS

Geary, C.H., "Laser Particulate Detector", *ImechE*, 1984, C39/84, 200–206.

* cited by examiner

Primary Examiner—Hezron Williams
Assistant Examiner—Nashmiya Fayyaz
(74) Attorney, Agent, or Firm—Joseph C. Wang; Paul E. Purwin

(57) ABSTRACT

A method for continuous monitoring the presence of entrained catalyst in a regenerator flue gas stream of a fluidized catalytic cracking unit is provided. The method has the following steps: (a) passing the regenerator gas stream through a separation system to remove a portion of the catalyst fines and to create a cleaner regenerator gas stream; (b) collecting a sample portion of the cleaner regenerator gas stream and directing the sample portion of the cleaner regenerator gas stream through an inertial separating device to separate entrained catalyst from the sample portion of the cleaner regenerator gas stream; (c) collecting any separated catalyst from the inertial separating device; and (d) monitoring the efficiency of the separation system by analyzing at least the amount of the collected separated catalyst or the particle size of the collected separated catalyst. An apparatus for measuring the amount of potentially erosive catalyst fines in a regenerator flue gas stream in a fluidized catalytic cracking unit is also provided. The apparatus is a sampling probe for collecting a sample portion of the regenerator flue gas from a line through which the regenerator flue gas stream flows, and an inertial separating device located downstream of the sampling probe and in fluid communication therewith, for removing any entrained catalyst fines from the sample portion of the regenerator flue gas.

6 Claims, 1 Drawing Sheet

PROCESS FOR DETERMINING THE AMOUNT OF EROSIVE MATERIAL ENTERING A POWER RECOVERY TURBINE

FIELD OF THE INVENTION

The present invention relates to measuring the character of particulate matter in a gas, and more particularly to measuring the character of particulate matter in a gas stream before entering a turbine.

BACKGROUND OF THE INVENTION

Methods and apparatus for measuring the concentration of particulate matter in a gas are well known. U.S. Pat. Nos. 4,531,402 and 5,571,945 describe such methods and devices, although they employ rather complex and costly systems. Consequently, these systems are not feasible or practical for use in all scenarios or for continuous or semi-continuous use.

Catalytic cracking is the backbone of many refineries. It converts heavy hydrocarbon feeds (gasoils) into lighter products by catalytically cracking large molecules into smaller molecules. Catalytic cracking operates at low pressures, without hydrogen addition, in contrast to hydrocracking, which operates at high hydrogen partial pressures.

In fluidized catalytic cracking (FCC), the cracking catalyst, having an average particle size of about 50–150 microns, circulates between a cracking reactor (typically, a riser reactor) and a catalyst regenerator. In the reactor, the gasoil feed contacts the heated catalyst that exits the regenerator section. This hot catalyst vaporizes and cracks the feed at approximately 425° C.–600° C.

The cracking reaction deposits carbonaceous hydrocarbons, or coke, on the cracking catalyst, thereby partially deactivating the active zeolite sites on the catalyst. The cracked products are separated from the coked catalyst in a disengager section, typically by means of a cyclone system. The separated coked catalyst is then stripped of volatiles, generally by contact with steam, and this stripped catalyst is then regenerated within the regenerator through oxidation with oxygen containing gas, usually air, to burn coke from the catalyst.

This regeneration step restores the activity of the cracking catalyst and simultaneously heats the catalyst to approximately 500° C.–900° C. This heated catalyst is recycled to the cracking reactor to catalytically crack the incoming gasoil feed. A flue gas which is formed by burning the coke in the regenerator is usually treated for removal of particulates and sometimes for conversion of carbon monoxide, after which the flue gas is normally discharged into the atmosphere. Prior to discharge, however, a portion of the energy contained in the flue gas stream can be recovered by using a power recovery turbine.

To be profitable, modern FCC units must run at high throughput, and run for extended periods of time, typically more than one year between shutdowns. Much of the output of the FCC unit is further processed in downstream operating units. A significant fraction of a refinery's gasoline pool is usually derived directly from the FCC unit. It is important that the unit operate reliably for years, and be able to accommodate a variety of gasoil feeds, including very heavy gasoil feeds. The unit must operate without exceeding emissions limits on pollutants or particulates. The cracking catalyst is relatively expensive, and most units have several hundred tons of catalyst in inventory within the FCC unit at one time. Most FCC units circulate tons of catalyst per minute, the large circulation being necessary because the feed rates are large; indeed, roughly five tons of catalyst are required to crack every ton of oil.

If these large amounts of catalyst are not removed from cracked products exiting the reactor section of the FCC unit, the heavy hydrocarbon products become contaminated with catalyst, particularly the smaller particle size catalytic materials, or "fines." These fines must also be removed from the flue gas that is discharged from the regenerator. Any catalyst not recovered by the cyclone separation system within the regenerator stays associated with the flue gas, unless an electrostatic precipitator, bag house, or some sort of removal stage is added. The amount of fines in most FCC flue gas streams exiting the regenerator is enough to cause severe erosion of the blades of the power recovery turbine if one is used to recover some of the energy in the regenerator flue gas stream.

These solid catalytic fines that exit the regenerator are entrained in the regenerator flue gas stream and are exceedingly difficult to remove, as evidenced by their passing through several stages of highly efficient cyclones. These fines are very small; typically, most of the fines are below 40 microns and some under 5 microns.

Recovery of these catalyst fines has been a challenge since the initial use of FCC units. Refineries with large FCC units typically use 6–8 primary and 6–8 secondary cyclones in their FCC regenerators, and are limited due to mechanical constraints and concerns of excessive pressure drops. This series of cyclones inherently allows a large amount of catalyst fines to pass out with the regenerator flue gas. This material must be removed from the flue gas prior to discharge to the atmosphere or passage through a power recovery turbine.

Generally, a third stage separator is installed upstream of the turbine to reduce the quantity of catalyst fines in the fluid stream to thereby protect the turbine blades, or permit discharge of flue gas to the air. When a third stage separator is used, a fourth stage separator is typically used to process the underflow from the third stage separator.

Accordingly, the amount and size of catalyst fines that can cause damage to the turbine is limited by the use of inertial separating devices upstream of the turbine. These inertial separators are also subject to erosion and other modes of damage that reduce their efficiency. It is, therefore, desirable to provide a device that can be used to monitor the condition of the inertial separators that are used to protect the turbine.

The most damaging particles that enter the turbine are those that are greater than five microns in diameter. These are normally removed by a well designed, efficient, inertial separating system. Therefore, their presence at the inlet to the turbine is indicative of some degree of failure of the inertial separator system.

Current methods of determining the amount of potentially damaging particles entering the turbine have attendant drawbacks. Optical devices measure the amount of light scattered by the particulates in the flue gas. These require either sample conditioning or probe cooling to protect the delicate optical devices. Optical devices also require frequent cleaning of the optics and are more sensitive to the smaller particles than they are to the larger, more damaging particles. It is, therefore, desirable to provide an apparatus for measuring the amount of erosive material in a gas stream that is reliable, relatively inexpensive to operate and maintain, sensitive to relatively large particles and can withstand relatively harsh environmental conditions of the gas stream.

Catalytic cracking units are operated continuously for periods of up to five years. During this time, the unit might experience several periods of abnormal operation, or upsets. If these upsets cause excessive catalyst losses or cause the third stage separator to lose efficiency, then they can also cause accelerated wear of the power recovery turbine blades. Batch sampling usually misses these upsets because the unit is operated smoothly during scheduled testing. To predict the amount of wear in a power recovery turbine, it is important to know the total cumulative exposure to particles larger than about 10 microns. This information can only be obtained with a sampling system that is in continuous or at least semi-continuous operation, where the actual sampling time is at least 10 times the sampling recovery time and where the off-line time for sample recovery is relatively short.

Barrier filter devices extract a portion of the flue gas and pass the sample through a filter or liquid impinger to collect the particulates in the gas stream. The recovered material must then be analyzed to determine the amount of large particles in the sample. These devices must be operated batch-wise and the filters are subject to plugging and tearing, while the liquid in the impinger evaporates at normal flue gas temperatures. This is a labor intensive operation and the accuracy of the procedure depends on both the mass and particle size distribution of the recovered sample. It is, therefore, desirable to provide an apparatus for determining the amount of erosive material entering a power recovery turbine that works according to a simple mechanism, can be operated continuously or semi-continuously, and accordingly, has relatively low labor, maintenance and operating costs.

SUMMARY OF THE INVENTION

A method for monitoring the presence of entrained catalyst in a regenerator flue gas stream of a fluidized catalytic cracking unit is provided. The method comprises the following steps: (a) passing the regenerator gas stream through a separation system to remove a portion of the catalyst fines and to create a cleaner regenerator gas stream; (b) collecting a sample portion of the cleaner regenerator gas stream and directing the sample portion of the cleaner regenerator gas stream through an inertial separating device to separate entrained catalyst from the sample portion of the cleaner regenerator gas stream; (c) collecting any separated catalyst from the inertial separating device; and (d) monitoring the efficiency of the separation system by analyzing at least the amount of the collected separated catalyst or the particle size of the collected separated catalyst.

An apparatus for measuring the amount of catalyst fines in a regenerator flue gas stream in a fluidized catalytic cracking unit is also provided. The apparatus comprises a sampling probe for collecting a sample portion of the regenerator flue gas from a line through which the regenerator flue gas stream flows, and an inertial separating device located downstream of the sampling probe and in fluid communication therewith, for removing any entrained catalyst fines from the sample portion of the regenerator flue gas.

In an alternate embodiment of the present invention, the apparatus further comprises a vacuum source located downstream of the inertial separating device for creating negative pressure to take the sample of gas and run it through the apparatus. In a preferred embodiment of the present invention, the sampling probe is an isokinetic sampling probe, the inertial separating device is a cyclone, and the vacuum source is a steam ejector.

Preferably, the flue gas stream flows in a direction, and the isokinetic sampling probe comprises a pipe having an opening directed against the direction of the flue gas stream. In another preferred embodiment, the apparatus of the present invention further comprises a sample container located below the cyclone for collecting the particulate matter removed from the sample of gas.

Although the apparatus of the present invention is described throughout the specification in the context of measuring the amount of catalyst fines in a regenerator flue gas stream in a fluidized catalytic cracking unit, the apparatus is also provided for the general application of measuring the amount of particulate matter in a gas.

DETAILED DESCRIPTION OF THE PREFERRED EMBODIMENTS

Figures 1, 1A:
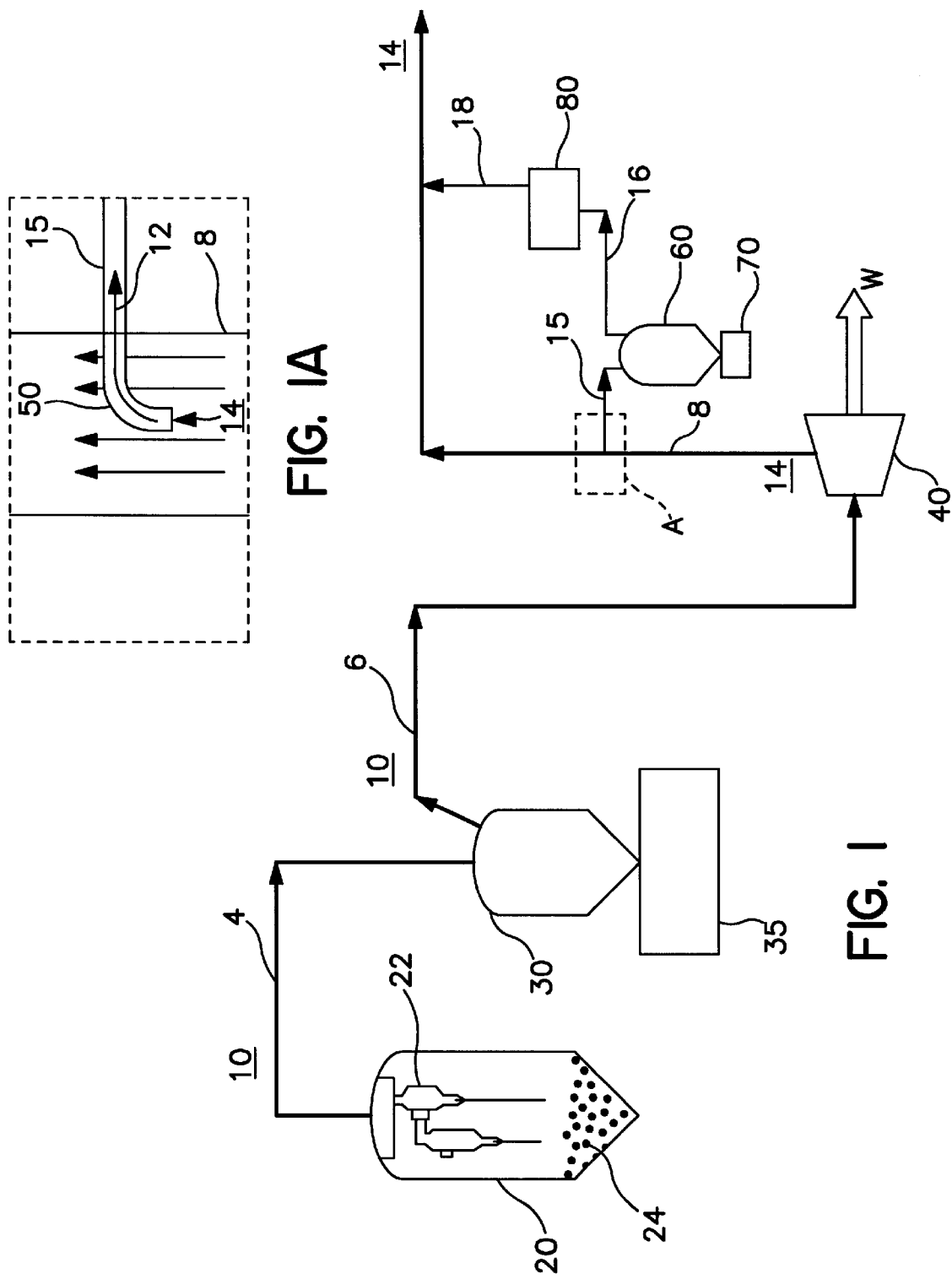
FIG. 1 is a schematic of a flue gas stream in cooperation with a preferred embodiment of the present invention.
FIG. 1A is a is an enlarged schematic of section A in FIG. 1.

The present invention provides an apparatus and method for determining the amount of erosive material entering a power recovery turbine in an FCC flue gas stream. The invention works by utilizing the inertia of the erosive particles and provides a direct indication of the amount of damaging material that is present in the flue gas stream.

Referring to the drawings, there is shown in FIG. 1 a regenerator flue gas stream 10 of a fluidized catalytic cracking (FCC) unit that is processed in accordance with a preferred embodiment of the present invention. The basic components of the process system shown in FIG. 1 include a regenerator 20, a flue gas stream 10 and a separation vessel 30. Vessels 20 and 30 each contain a cyclone filtration system 22 (representatively shown inside vessel 20). A power recovery turbine 40 is used to recover some of the energy in the flue gas stream 10.

In the normal course of operation of an FCC unit, coke is oxidized from the surface of the cracking catalyst with air within the regenerator 20. Thus, within the regenerator 20 there is found a gaseous stream containing the products of this oxidation process. Entrained within this gaseous stream are catalyst particles, or "fines." A first and second stage separation process is conducted directly within the regenerator section 20 of the FCC unit in an attempt to remove a substantial portion of the fines for the flue gas stream that is to exit the regenerator 20. However, this separation process, which is usually a cyclone separation system, does not remove all of the fines from the regenerator flue gas 10.

In the embodiment depicted in FIG. 1, the next stage of the separation process is separating vessel 30, referred to as the third stage separator, which typically contains anywhere from approximately 3 to several hundred smaller diameter cyclones, i.e., smaller than the cyclones of the first two stages. As the flue gas stream 10 flows through the cyclones in the third stage separator 30, separated catalyst fines settle on the bottom of the vessel 30 and accumulate in a catalyst hopper 35 located beneath the vessel 30. A fourth stage separator (not shown) may be used for further separation of catalyst fines and recovery in its catalyst hopper. The third stage catalyst hopper 35 is emptied periodically and the rate of accumulation of catalyst is used to monitor the efficiency of the separation devices upstream of the third stage separator. As shown in this system, cleaner flue gas stream 10 then proceeds via line 6 to the power recovery turbine 40. Generally, after this stage, the preferred weight percentage of fines in the stream 10 is less than 0.1 wt %, and more preferably less than 0.01 wt %.

The flue gas stream 10 enters the power recovery turbine 40 at a typical pressure of approximately 15 to 50 psig and a typical temperature of approximately 650–760° C. The flue gas stream 10 flows through the turbine section causing the turbine blades to rotate, thereby creating work W. Typically, the rotating turbine blades turn the rotor, which is connected to a generator for producing electricity or to a blower for supplying air to the regenerator 20. The exhaust 14 from the turbine 40 enters additional separation and/or pollution control devices (not shown) before being discharged into the atmosphere.

One pollution control device can be a carbon monoxide boiler that burns the carbon monoxide into carbon dioxide. Another pollution control device can be a waste heat boiler. One separation/pollution control device can be an electrostatic precipitator, which is designed to remove some of the catalyst fines.

The quantity and particle size distribution of the catalyst fines entering the turbine 40 or in the turbine exhaust 14 can be monitored by the apparatus of the present invention. In one embodiment, the apparatus comprises a sampling probe 50 for taking a sample 12 of flue gas 14, an inertial separating device 60 to remove particulates from the sample 12 of the flue gas, and a vacuum source 80 for creating negative pressure to take the sample 12 of flue gas and run it through the apparatus. FIG. 1A is an enlarged view of section A in FIG. 1 at the junction between lines 8 and 15. The sampling probe 50 is preferably an isokinetic sampling probe that can be a tube or pipe with an opening directed against the direction of the flow of the flue gas stream 14. The diameter of a typical probe 50 is approximately ½ inch where the flue gas line 8 is approximately 24 inches to 80 inches in diameter.

The sample 12 is removed from line 8 via line 15 to the inertial separating device 60 to separate any larger entrained catalyst fines. The inertial separating device can be any gravity, momentum or centrifugal separator. Preferably, the inertial separating device is a cyclone 60. The inertial separating device 60 has a sample container 70 attached to the bottom of the device 60 for collecting the catalyst fines that are removed from the flue gas sample 12. The vacuum source 80 is preferably a steam ejector 80 because of its reliability and relatively inexpensive cost. A cyclone 60, preferred for the same reasons and designed for the flow rate of the flue gas stream 10 of the particular FCC unit. The size and capacity of the cyclone 60 then dictates the size of the probe 50 and ejector 80.

The ejector 80 creates suction that allows the probe 50 to pull in a sample 12 of gas from the flue gas stream 14. The flue gas sample 12 is then directed into the cyclone 60, via line 15, where catalyst fines are removed and accumulate in the container 70. The cleaner flue gas 12 then exits the cyclone 60 via line 16 and flows through the ejector 80 and then is placed back into the flue gas stream 14 via line 18. The container 70 is emptied periodically and the rate of accumulation and particle size distribution of catalyst fines is used to measure the amount of erosive material entering the turbine 40. The rate of accumulation of the catalyst fines and their particulate size distribution is also used to monitor the efficiency of the separation devices upstream of the turbine 40.

The sampling probe 50 can be placed upstream or downstream of the turbine 40. If the probe 50 is placed upstream of the turbine 40, no vacuum source 80 is needed because of the relatively large pressure of the flue gas 10 upstream of the turbine 40. Preferably, the flue gas sample 12 should be returned to the flue gas stream 14 at any point downstream of where the probe 50 is placed.

The apparatus of the present invention provides a direct indication of the amount of damaging material that is present in the FCC flue gas stream 10 because it uses the same physical principles to collect the material that cause damage to the turbine 40, i.e., the inertia of the particles. Because the apparatus works according to a simple mechanism, it is reliable, relatively inexpensive to operate and maintain, sensitive to relatively large particles that can cause the most damage to the turbine 40 and can withstand relatively harsh environmental conditions of the flue gas stream 10 and 14.

It is to be understood that even though numerous characteristics and advantages of the present invention have been set forth in the foregoing description, together with details of the structure and function of the invention, the disclosure is illustrative only. For example, although designed for use in an FCC flue gas system, the present invention can be used to measure the amount of particulate matter in any gas stream or any gas. Accordingly, changes may be made in detail, especially in matters of shape, size and arrangement of parts within the principles of the invention to the full extent indicated by the broad general meaning of the terms in which the appended claims are expressed.

What is claimed is:

1. A method for monitoring the presence of entrained catalyst in a regenerator flue gas stream of a fluidized catalytic cracking unit, comprising the following steps:

(a) creating a regenerator gas stream within a regenerator section of a fluidized catalytic cracking unit, said regenerator gas stream comprising entrained catalyst;

(b) passing the regenerator gas stream from the regenerator through a separation system to remove at least a portion of the catalyst and to create a cleaner regenerator gas stream;

(c) applying suction to the cleaner regenerator gas stream to remove a sample portion therefrom;

(d) directing said sample portion of the cleaner regenerator gas stream through an inertial separating device to substantially separate entrained catalyst from the sample portion of the cleaner regenerator gas stream, thereby obtaining a substantially catalyst-free gas stream;

(e) collecting separated catalyst from the inertial separating device; and (f) monitoring the efficiency of the separation system by determining the amount of the collected separated catalyst or the particle size of the collected separated catalyst.

2. The method of claim 1, wherein the method is for at least semi-continuous monitoring of the presence of entrained catalyst and wherein said step of collecting any separated catalyst from the inertial separating device is performed periodically.

3. The method of claim 2, wherein said step of collecting any separated catalyst from the inertial separating device is performed at intervals of at least one day.

4. The method of claim 2, wherein said step of collecting any separated catalyst from the inertial separating device is performed at intervals of at least one week.

5. The method of claim 1 further comprising the step of returning the substantially catalyst-free gas stream back to the cleaner regenerator gas stream.

6. The method of claim 1 further comprising the step of passing the cleaner regenerator gas stream through a power recovery turbine before the step of applying suction to the cleaner regenerator gas stream.

* * * * *